(12) United States Patent
Sayed Sayed Ahmed et al.

(10) Patent No.: US 11,819,023 B2
(45) Date of Patent: Nov. 21, 2023

(54) POLYVINYL ALCOHOL/CHITOSAN COMPOSITE SOLUBLE ELECTROSPUN NANOFIBERS FOR DISINFECTANT ANTI-BACTERIAL AND ANTI-CORROSION APPLICATIONS

(71) Applicant: The American University in Cairo, New York, NY (US)

(72) Inventors: Wael Mamdouh Sayed Sayed Ahmed, Cairo (EG); James Kegere, Sironko (UG)

(73) Assignee: The American University in Cairo, New York, NY (US)

( * ) Notice: Subject to any disclaimer, the term of this patent is extended or adjusted under 35 U.S.C. 154(b) by 0 days.

(21) Appl. No.: 16/349,393

(22) PCT Filed: Nov. 15, 2017

(86) PCT No.: PCT/US2017/061762
§ 371 (c)(1),
(2) Date: May 13, 2019

(87) PCT Pub. No.: WO2018/093870
PCT Pub. Date: May 24, 2018

(65) Prior Publication Data
US 2019/0327966 A1 Oct. 31, 2019

Related U.S. Application Data

(60) Provisional application No. 62/424,363, filed on Nov. 18, 2016.

(51) Int. Cl.
| | | |
|---|---|---|
| *A01N 43/16* | (2006.01) | |
| *A01N 25/02* | (2006.01) | |
| *C23F 11/173* | (2006.01) | |
| *D01D 5/00* | (2006.01) | |
| *D01F 8/02* | (2006.01) | |
| *D01F 8/16* | (2006.01) | |

(52) U.S. Cl.
CPC ............ *A01N 43/16* (2013.01); *A01N 25/02* (2013.01); *C23F 11/173* (2013.01); *D01D 5/0007* (2013.01); *D01F 8/02* (2013.01); *D01F 8/16* (2013.01); *D10B 2401/13* (2013.01)

(58) Field of Classification Search
CPC ...... A01N 43/16; A01N 25/02; D01D 5/0007; D01F 8/02; D01F 8/16; C23F 11/173; D10B 2401/13
USPC .......................................................... 514/55
See application file for complete search history.

(56) References Cited

U.S. PATENT DOCUMENTS

2013/0165487 A1* 6/2013 Arthur ................... A01N 43/78
514/365

FOREIGN PATENT DOCUMENTS

| CN | 104046667 A | * | 9/2014 |
| KR | 2001-0027073 | * | 4/2001 |
| RU | 2468129 | | 7/2012 |
| WO | WO 2015/131144 A1 | * | 9/2015 |

OTHER PUBLICATIONS

Seo et al.; KR2001-0027073 B1; Apr. 6, 2001 (Machine-English Translation).*
Tianjin Tiens Biological Development Co Ltd ; CN 104046667 A; Sep. 17, 2014 (Machine-English Translation).*
Baker et al. A review of polyvinyl alcohol and its uses in cartilage and orthopedic applications. J. Biomed. Materials Research Part B vol. 100B No. 5, online publication Apr. 19, 2012 pp. 1451-1457.
Vimala et al. Fabrication of Curcumin Encapsulated Chitosan-PVA silver Nanocomposite Films for Improved Antimicrobial Activitiy. J. Biomat. and Nanobiotechn. vol. 2(1) Jan. 2011 pp. 55-64.

* cited by examiner

*Primary Examiner* — Layla D Berry
(74) *Attorney, Agent, or Firm* — LUMEN PATENT FIRM (57) ABSTRACT

A natural liquid composition is provided for disinfectant, antibacterial or anticorrosion applications. The natural liquid composition is an electrospun solubilized composition of natural chitosan (CS) and an FDA approved polymer polyvinyl alcohol (PVA). Two fillers, citric acid (CA) and ascorbic acid (AA), added anti-corrosion property to the composite nanofiber solution without affecting the other properties (disinfectant and antibacterial) and have a final synergistic effect of all components together in a final solution form. Embodiment of the invention advances the art by providing a natural solution to overcome at least some of the problems with the currently used agents.

2 Claims, 8 Drawing Sheets

POLYVINYL ALCOHOL/CHITOSAN COMPOSITE SOLUBLE ELECTROSPUN NANOFIBERS FOR DISINFECTANT ANTI-BACTERIAL AND ANTI-CORROSION APPLICATIONS

CROSS-REFERENCE TO RELATED APPLICATIONS

This application is a 371 of PCT application PCT/US2017/061762 filed Nov. 15, 2017. PCT application PCT/US2017/061762 claims the benefit of U.S. Provisional application 62/424,363 filed Nov. 18, 2016.

FIELD OF THE INVENTION

This invention relates to natural liquid compositions for disinfectant, anti-bacterial and anti-corrosion applications.

BACKGROUND OF THE INVENTION

Bacterial infections in health facilities are one of the key challenges facing humanity today and this is worsened by the current trend of anti-biotic resistance and resistance to natural controls through different adaptive mutations. Currently, disinfection is done through the use of powerful chemical agents which come with harmful side effects to both human health and the environment. Certain sensitive areas are risky to use such as harsh chemicals as a safety precaution. Food production chains, theaters, foods, and baby feed bottles among others and in case powerful chemicals are used in these areas, copious amounts of water have then to be used to lower the risks associated with them. The use of natural materials would be desired which bare no harm to human cells and are in essence innocuous to human health. Natural compounds not only have antibacterial effect, but also posses important properties such as prebiotic activity for eukaryotic cells, anti-oxidant activity, anti-rust and pro-environment properties. Although research into natural remedies are ongoing, however, fewer products have yet been put into the market to counter the challenges faced. This is partly due to the unpredictability and the long list of undefined natural compounds whose discovery takes a tortuous route as compared with conventional chemicals. The present invention advances the art by providing a natural solution to overcome at least some of the current problems with the current agents used for disinfectant, anti-bacterial and/or anti-corrosion applications.

SUMMARY OF THE INVENTION

This invention focused on the fabrication of natural polysaccharide (chitosan, CS) composite electrospun nanofibers mixed with other FDA approved materials like polyvinyl alcohol (PVA), (in some variations also with citric acid (CA) and ascorbic acid (AA) used as fillers) and solubilize the produced nanofibers to be used as natural liquid disinfectant and antibacterial as well as anticorrosive agent. The main challenge in this invention was to fabricate a composite that has purely natural and FDA approved materials, and yet overcome the conventional disinfectants in the market which have major drawbacks, and more importantly is to make a liquid solution of the fabricated electrospun composite nanofibers to be applied directly in different surfaces such as floors, walls and machineries without causing any side effects to the users.

In one example, the PVA/CS composite nanofibers of this invention were fabricated with an in-house electrospinner instrument using high applied voltage between 15-24 KV with a solution flow rate of 1 mL/hr with nanofiber diameter in the nanometer scale. The nanofibers were then dissolved in 5% CA and AA and soluble liquid solution was prepared for antibacterial studies against Gram positive and Gram negative bacteria. These composite nanofiber solution showed enhanced antibacterial activity when tested against *Escherichia coli* (*E. coli*) and *Staphylococcus aureus* (*S. aureus*) with an inhibition rate of up to 95%. To the best of our knowledge, liquid solutions of natural composite nanofibers have not been reported before in the literature. This composite nanofiber solution liquids open new avenues towards using natural nanotechnology-based material acting as strong disinfectant and anticorrosive agents.

In another example, a natural liquid composition is provided for disinfectant, antibacterial or anticorrosion applications. The natural liquid composition is an electrospun solubilized composition of natural chitosan (CS) and an FDA approved polymer polyvinyl alcohol (PVA). Two fillers, citric acid (CA) and ascorbic acid (AA), added anticorrosion property to the composite nanofiber solution without affecting the other properties (disinfectant and antibacterial) and have a final synergistic effect of all components together in a final solution form. Embodiment of the invention advances the art by providing a natural solution to overcome at least some of the problems with the currently used agents. In a preferred embodiment, the PVA and CS have a ratio of about 8:2. The molecular weight of the PVA is about 125000 and for the CS the molecular weight is low (about 110 cg and degree of deacetylation of about 89.9%; cg stands for Cosmetic Grade and 110 cg equals to about 200 Kilodalton [kDa] (as per product datasheets by Primex, Inc).

BRIEF DESCRIPTION OF THE DRAWINGS

FIGS. 2A-F show according to an exemplary embodiment of the invention SEM images of PVA:CS Nano fibers electrospun at solution flow rate of 1 mL/hr and applied voltage of 16 kv from PVA solutions concentration (w/w): FIG. 2A 6%, FIG. 2C 8% and FIG. 2E 12%, (w/w), respectively, with their respective size distribution histograms in FIG. 2B, FIG. 2D and FIG. 2F.

DETAILED DESCRIPTION

For the purposes of the present invention, the technique of electrospinning of natural composite nanofibers is used. An electrospinner is an equipment that utilizes applied high voltage with the help of a syringe pump to control solution feed rate, leading to the ejection of the polymeric composite materials through the spinneret of the needle, with the charges acquired on the polymers in the needle overcome by the electrostatic repulsion of the current, with strong momentum forming a cloud of electrospun nanofibers that are then grounded on the collector located at a short distance from the end of the spinneret.

The formed nanofibers have variations in size, length, integrity and bead formation and these are governed by the applied parameters which are either solution based or electrospinning parameters. Solution parameters are those that characterize the material being electrospun. These include viscosity which is impacted on partly by the concentration of the material being used, conductivity of the material which is governed by the nature of the charges on the polymer composite, and the temperature of the fed solution. Electrospinning parameters are the parameters that are used and adjusted on the equipment during the process of electrospinning, including the high applied voltage, solution feed rate, and the distance between the spinneret and the plate collector. Ambient parameters like humidity and temperature of the electrospinner have a significant role they play in the resulting nanofibers. Electrospinning has been limited mostly to synthetic polymers as these are easily defined in properties than natural polymers. Embodiments of this invention are based on FDA approved polyvinyl alcohol (PVA) and natural polysaccharide as chitosan (CS) resulting in a natural composition liquid that is biocompatible, biodegradable, non-toxic, dissolve in organic acid. In one example, PVA and CS are formed in a combination at a ratio of about 8:2 which is a near uniform beadles nanofiber electrospun liquid composition.

To form uniform electrospun nanofibers prepared from mixed solutions of PVA and CS, it is the ratio (either volume/volume or gram/gram) of the mixed solution that affects the spinnability and quality of the fabricated nanofibers. In this regard, different mixing ratios were prepared (PVA/CS) ranging between (10:0, 9:1, until 0:10). PVA is the main source that helps the ejection of the solution out of the needle to form nanofibers. More importantly, the higher the PVA content, the easier nanofibers will form. In addition, CS solution alone is very difficult to be electrospun alone without the presence of a polymer like PVA or polyethylene oxide (PEO) for example, which help in the ejection of the mixed solution. In this regard, the best PVA/CS ratio that led to the formation of uniform and bead-free nanofibers were about 8:2.

CS is characterized by its molecular weight (MW) or degree of Deacetylation which greatly affect its properties and applications. The supplier of CS used in this invention offers three different MW with different degree of Deacetylation (DD): low MW (110 cg with 89.9% DD), medium MW (400 cg with 84.8% DD) and high MW (1600 cg with 76% DD), respectively. The MW and degree of Deacetylation of CS that were used in this invention were low MW (110 cg) and 89.9% for DD. Cg stands for Cosmetic Grade and 110 cg equals to about 200 Kilodalton [kDa], 400 Cg equals to about 275 kDa, and 1600 Cg equals to about 350 kDa (as per product datasheets by Primex, Inc).

It is worth mentioning that all other PVA/CS ratios other than about 8:2 did not allow the formation of uniform and bead-free nanofibers.

Chitosan has strong anti-microbial activity against both gram positive and gram negative bacteria, viruses and fungi. It has attracted great attention in the last two decades for biomedical applications given the novelty chitosan has as pertains to its properties. The mechanism of chitosan anti-microbial action is still not clear, however research has linked the polycationic nature of the amine groups which in solution lowers PH below 6.5 as being one of the main factors behind its anti-microbial efficiency. The cations on the biopolymer is therefore believed to interact with negatively charges on the cell membrane of microorganisms and thus affecting the physiological processes of the cell. Other findings indicate that lower molecular weight [SUCH AS MW xx-yy] chitosan diffuses into the bacterial cells and attach to the DNA thereby inhibiting the process of RNA synthesis. Moreover, among different categories of polysaccharides, CS offers the greatest antibacterial activities against different bacterial strains.

The following is an exemplary embodiment of methods and materials used.

Materials and Methods

Polyvinyl alcohol (PVA MW 125000, 20-98% hydrolysis) was purchased from Sigma Aldrich Europe. Chitosan (low MW 400 cg, with 89.9% degree of deacetulation) was purchased from (Primex ehf, Chitoclear, Iceland). Difco LB agar broth media were obtained from Becton Dickson Company USA.

Preparation of PVA/Chitosan Nanofibers

PVA and CS were prepared by dissolving CS in 1% acetic acid and then adding to PVA dissolved in deionized water at varying mixing ratios. The results were obtained and these were largely controlled by the MW of CS, ratio adjustments and the applied voltage as discussed later in this section. At a high ratio of PVA:CS about (9:1 and 8:2), nearly beadles fibers were formed and this masked all the other factors that were at play. However, as the ratio of PVA in the mixture lowered below 7:3 (PVA:CS), difficulties in electrospinning observed and dropping from the needle tip increased. This was more in the mixture containing the medium molecular weight CS than that having the higher molecular weight CS provided the concentration of CS was maintained at 3% in 1% acetic acid solution.

Dissolution of PVA/Chitosan/Citric Acid/Ascorbic Acid

After successful fabrication of PVA/CS composite nanofibers, 0.2-1 mg of the nanofibers were dissolved in one liter of 5% of (Citric acid, Ascorbic acid, mixture of Citric and ascorbic acid at 1:1 ratio)/deionized water by gently shaking on a magnetic stirrer for 12 hours at 400 rpm. The resulting solution was standardized by homogenizing for 30 seconds before it was sterilized and readied for anti-microbial tests.

Commercial Disinfectant Solution in PVA/Chitosan (P.C.) Nanofiber Solution

This experiment was done to determine the effect of the nanofiber solution on the anti-bacterial activity of a selected commercially used disinfectant solution in a quest to reduce the amount of chemicals used and drift towards an environmentally sensitive disinfectant. In this process, 1% commercially used disinfectant in nanofiber solution was prepared by dissolving 0.1 mL of the commercially used disinfectant into 10 mL of composite nanofiber solution (PVA/CS/CA/AA) followed by slow mechanical shaking with vortex for 20 seconds. The mixture was then put in an Eppendorf and stored for antibacterial studies. Separately, 1% of the commercially used disinfectant in distilled water was also prepared to compare the efficiency of the two categories in the antibacterial study.

Chemical Characterization

Fourier Transform Infrared (FT-IR) spectroscopy (Nicolet 380-Thermo Scientific, USA was used to determine the functional chemical groups on the individual components and the composite nanofibers formed. The process involved preparation of discs made of potassium bromide (KBr) involving a disc compressor after thorough mixing of the samples with KBr pellets.

Morphological Characterization

To understand the uniformity, deformity and size of the nanofibers formed, Scanning Electron Microscope (SEM) (FESEM, Leo supra 55—Zeiss Inc., Germany) was used. Aluminum foils coated by the nanofibers measuring between 0.2 to 0.7 square centimeters were mounted to the stand and examined. For the dissolved nanofibers, a drop of the solution was dried on a foil in an oven at 40° C. for four hours. The discs were then gold sputtered and mounted on to the stand for examination.

Water Immersion Test

Nanofibers were immersed in warm distilled water at 37° C. for 2 and 24 hours. Then the composite nanofibers were immediately weighed after removing the surface water with filter paper. The degree of weight loss of composite nanofibers was calculated according to equation (1). The weight before immersion in water (wi) and after immersion in water and drying (wf) were measured.

$$\text{wt} \cdot \text{loss } \% = \frac{w_i - w_f}{w_i} \times 100 \quad (1)$$

Antimicrobial Assessment

The composite nanofibers were examined for their antibacterial activity against *E. coli* (ATCC 8739) and *S. aureus* (ATCC 6538) by using serial dilution method. In this method, colony forming units (CFU) were compared at the $6^{th}$ dilution between bacteria inoculum and bacteria/sample inoculum. The bacterial and bacterial/sample inoculums were prepared from a pre-culture of bacteria and sterilized sample (using U.V lamp for 55 minutes) and incubated for 24 hrs at 37° C. at 150 RPM. The samples were then diluted to the $6^{th}$ dilution which was then plated on LB agar media in petri dishes. The plated petri dishes were incubated at 37° C. for another 24 hrs after which formed colonies were formed.

Anticorrosion Test

The ability of the composite nanofiber solution to prevent rust was one of the most important tests for the formulated nanofiber solution as these would be applied on top of different surfaces and being in aqueous solution there could be a danger of causing rusting and more danger to health and systems performance. This experiment was conducted by placing iron nails into three separate solutions; Ammonium nitrate ($NH_4NO_3$), PVA/CS nanofiber solution, and a mixture between $NH_4NO_3$ and PVA/CS nanofiber solution. The three petri dishes were left exposed to oxygen supply in a dust-free laminar flow for 24 hrs and examination was carried out to assess the extent of rust on the nails.

Results

Figure 1A:
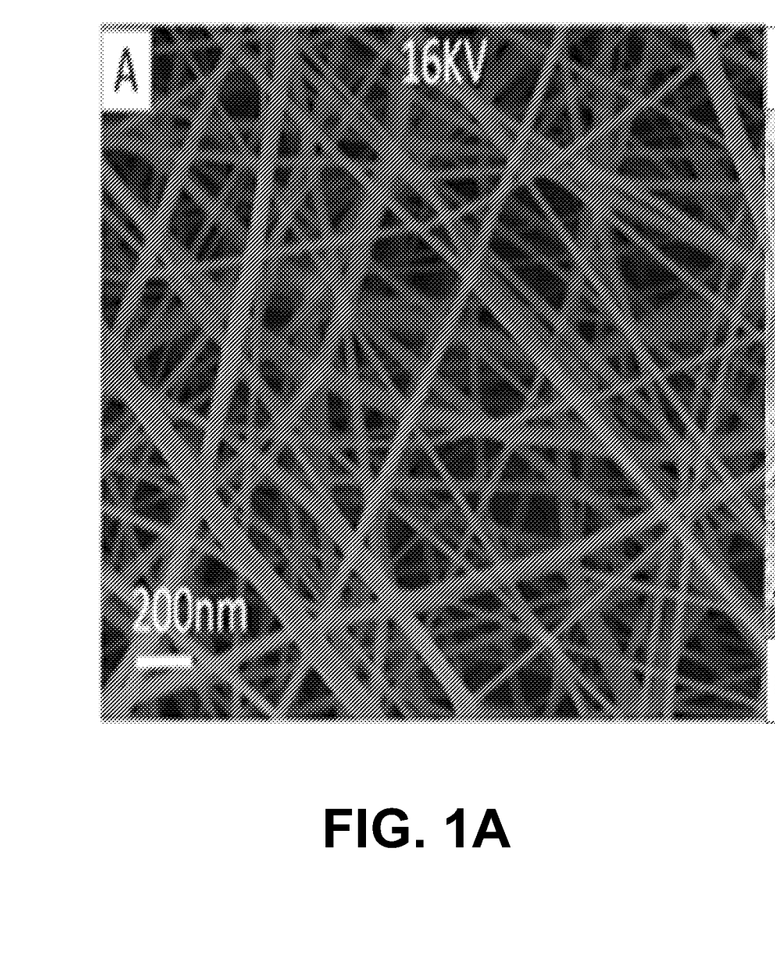
FIGS. 1A-B show according to an exemplary embodiment of the invention SEM images of (FIG. A) PVA:CS nanofibers, (FIG. B) PVA:CS nanofibers in solution.
Figure 1B:
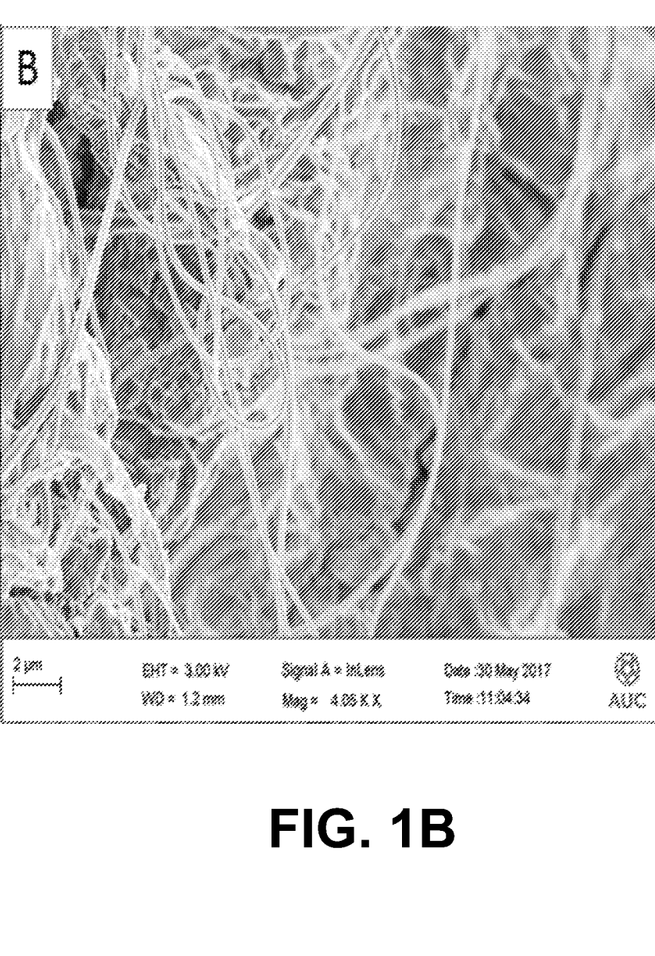
Figure 2A:
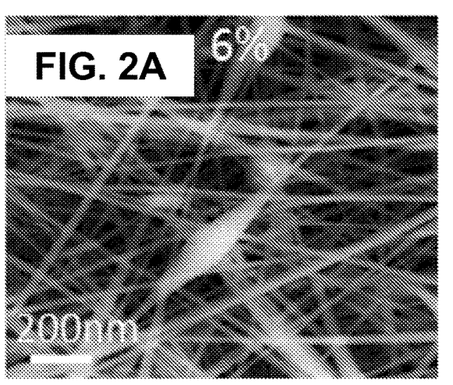
Figure 2B:
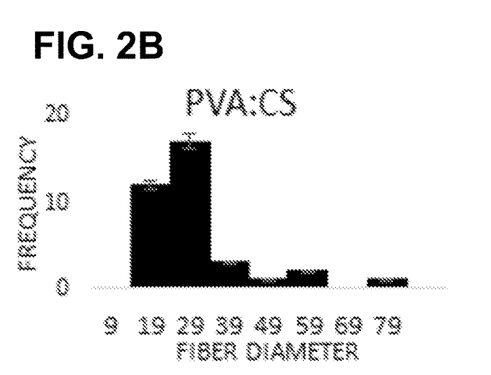
Figure 2C:
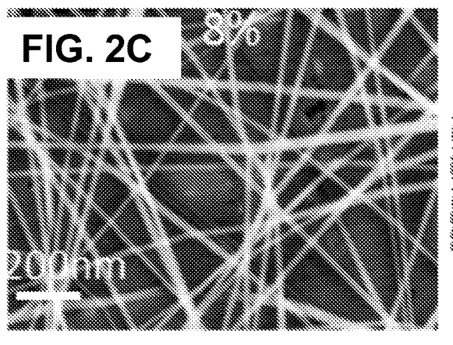
Figure 2D:
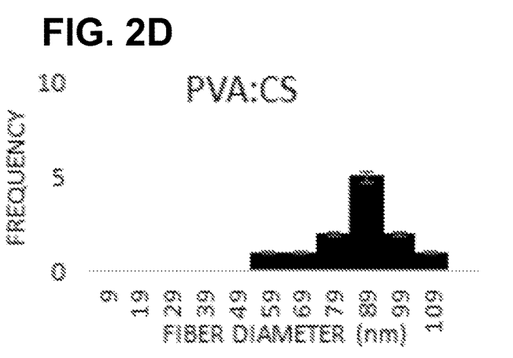
Figure 2E:
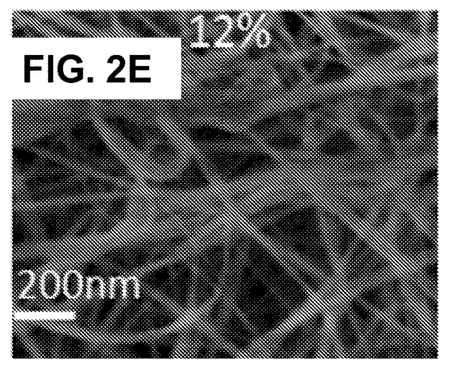
Figure 2F:
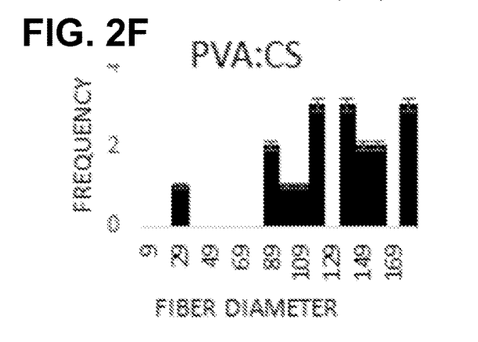
Figure 3A:
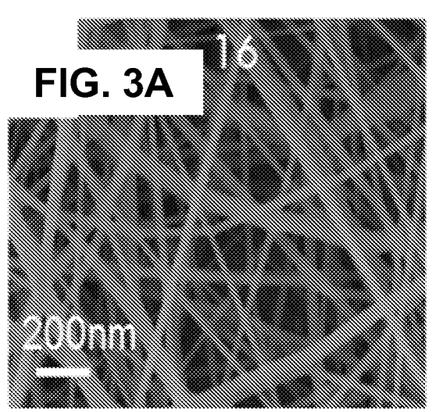
FIGS. 3A-F show according to an exemplary embodiment of the invention SEM images of PVA:CS nanofibers with effect of voltage FIG. 3A (16 kv), FIG. 3C (18 kv) and FIG. 3E (21 kv) on 8% solution flow rate of 1 mL/hr., tip to collector distance of 12 cm with their size distribution histograms in FIG. 3B, FIG. 3D and FIG. 3F.
Figure 3B:
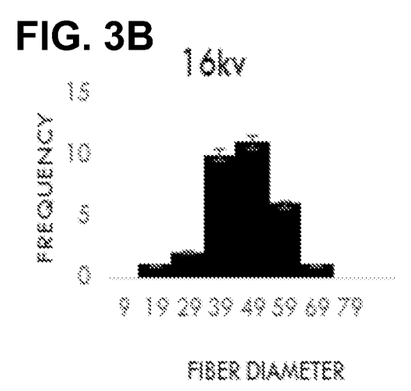
Figure 3C:
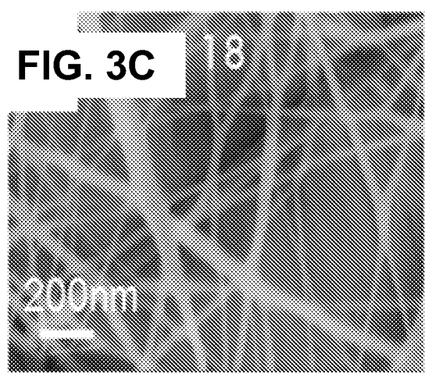
Figure 3D:
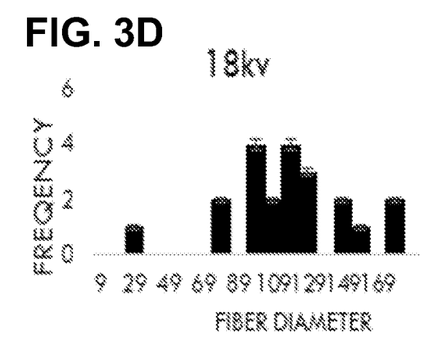
Figure 3E:
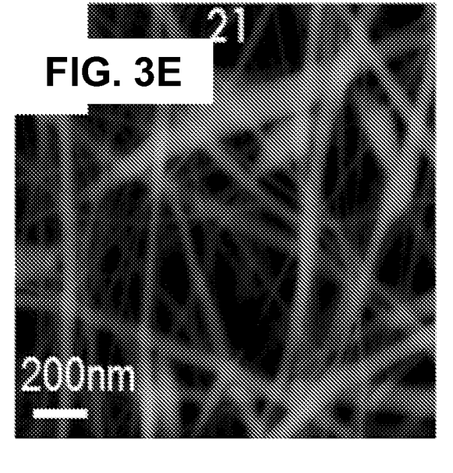
Figure 3F:
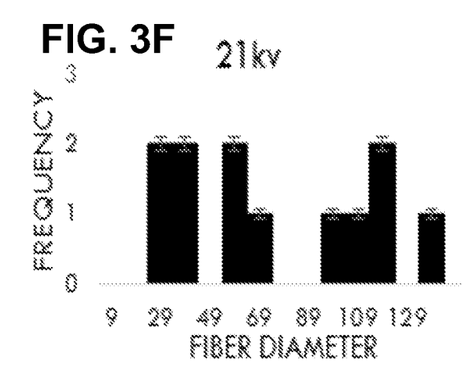
Figure 4A:
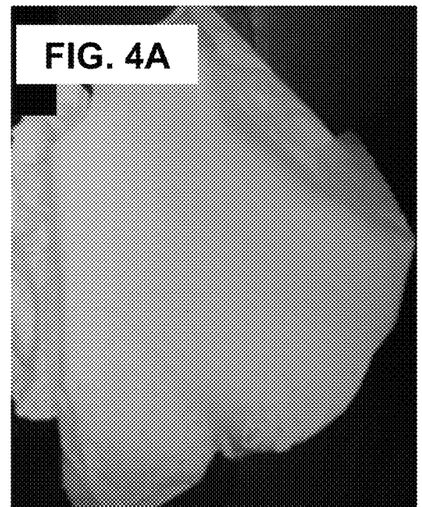
FIG. 4A-E show according to an exemplary embodiment of the invention an image of (FIG. 4A) a nanofiber mat, (FIG. 4B) a nanofiber suspension in solution, (FIG. 4C) dissolved nanofibers in solution, (FIG. 4D) and (FIG. 4E) SEM images of nanofibers in solution at different magnification.
Figure 4B:
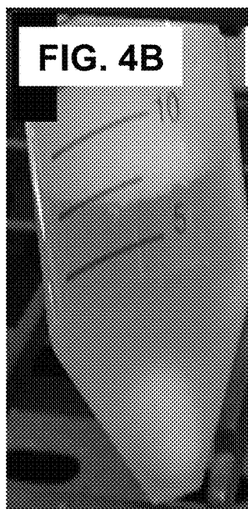
Figure 4C:
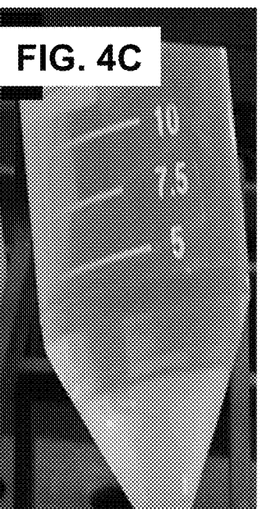
Figure 4D:
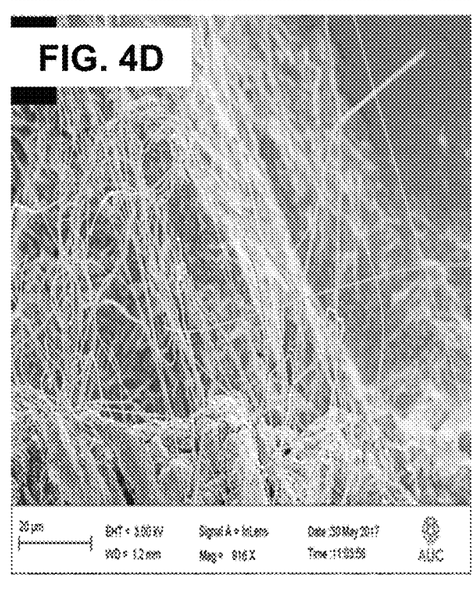
Figure 4E:
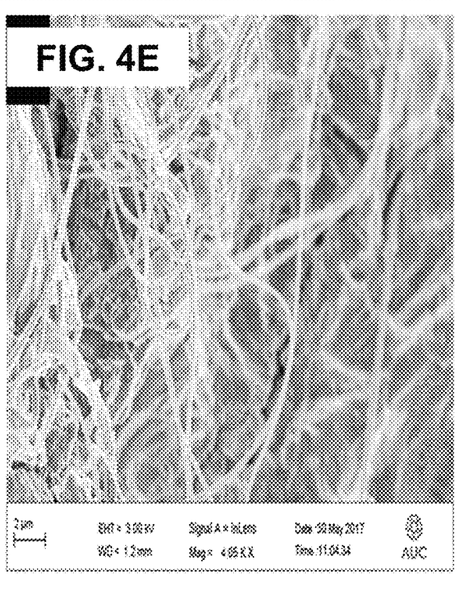

PVA/CS nanofibers were obtained after a series of parameter adjustments (FIGS. 1A-B). A number of factors that affect fiber formation were studied like the effect of solution concentration, solution feed rate and collector distance from the spinneret to the collection plate. Production of nanofibers was generally smooth with the PVA ratio higher than CS, nanofibers with uniform diameter distribution and smooth beadles entanglements were generated at an applied voltage range of 16-18 kv, solution feed rate range of 0.9-1.3 mL/hr, and a tip to collector distance between 13 to 15 cm.

Effect of Solution Concentration

Concentration of the solution is one of the key factors that determines the type of fibers that can be obtained by electrospinning. In order to study the influence of concentration on nanofiber formation, different solutions (PVA:CS) ratios were used as shown in the SEM images in FIGS. 2A-F. It was observed that the formation of smooth beadles fibers increases with increasing the concentration until reaching a maximum when further increase leads to the formation of ribbon like structures.

Effect of Voltage on In-Situ Mixtures.

Voltage variance was very effective on the formation of nanofibers and keeping other parameters constant it was observed that changes in the applied voltage drastically changes the properties of the nanofibers. At a low applied voltage, fibers with deformities and inconsistences resulted while at moderate applied voltage, there was a transition to smooth fibers with better diameter range distribution, minimum beads and integrity of the nanofibers. However, increasing the applied voltage supply was immediately consequential on the morphology of the nanofibers. At a 21 kv, beaded fibers were formed, and fibers were inconsistent in size and length (FIGS. 3A-F).

Effect of Fiber Dissolution in 5% Citric Acid

Dissolution of PVA/CS nanofibers in CA solution resulted first in a precipitate then with constant stirring at 400 rpm, a monophase solution was formed. When examined for the presence of nanofibers in the solution using SEM, fiber islands were observed with smoothly suspended fibers (FIG. 4). It was therefore clear that dissolution of the nanofibers did not particularly destroy the fibers albeit with disintegration and wide distribution in solution.

Fourier Transformation Infra-Red Spectroscopy

Figure 5:
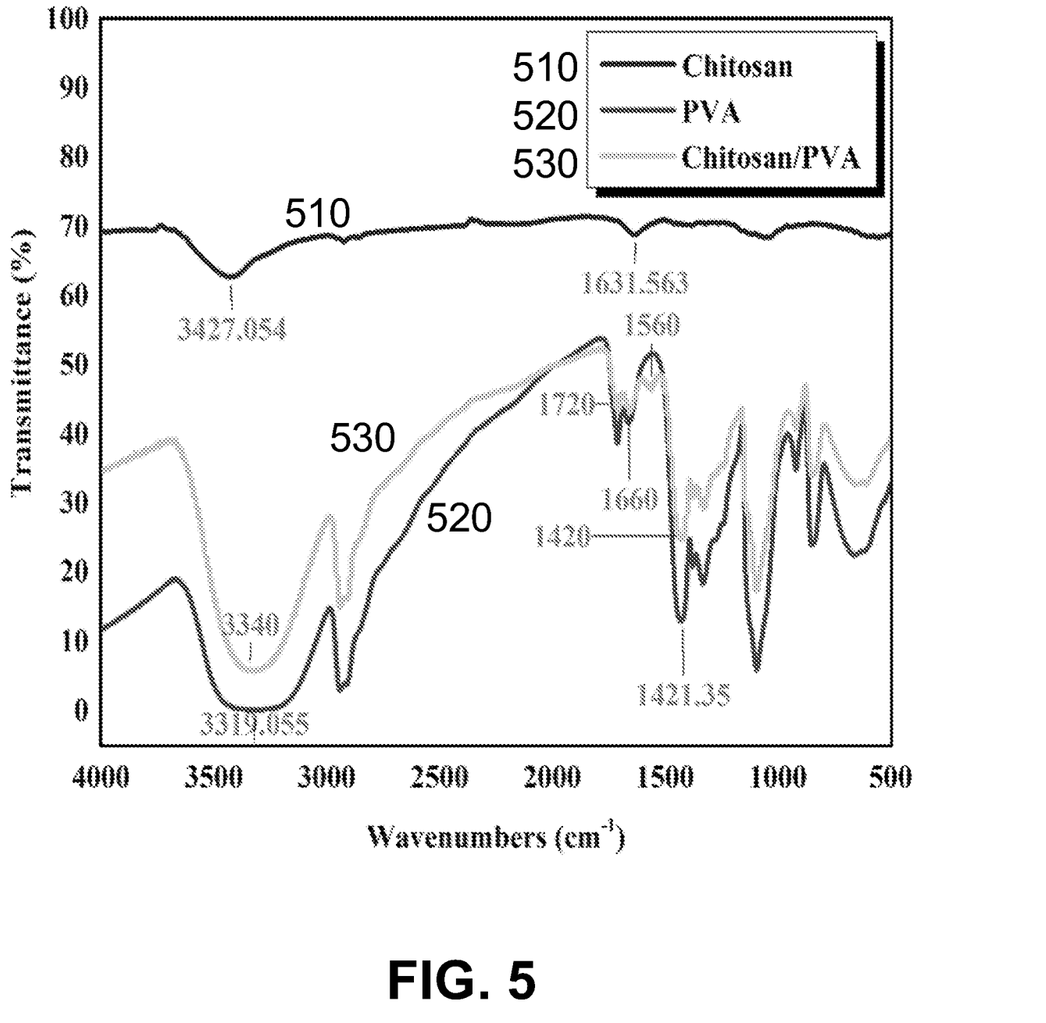
FIG. 5 shows according to an exemplary embodiment of the invention an FT-IR spectrum of the CS/PVA nanofibers in comparison with its starting materials; CS and PVA.

FT-IR was used to reveal the chemical changes when PVA interacted with CS to form the composite system as shown in FIG. 5. The chemical structure of the fabricated CS/PVA composite nanofibers was confirmed by FT-IR spectroscopy. Its representative FTIR spectra with comparison to its corresponding starting materials is shown in FIG. 5. The characteristic IR absorption bands of N—H and O—H stretching of CS and PVA found around 3427 $cm^{-1}$ and 3319 $cm^{-1}$, respectively were found to be overlapped forming a shifted broad absorption peak in the resulting CS/PVA composite nanofibers. This might be due to the hydrogen bonding formed between the OH and NH groups of both blended materials. Additionally, the characteristic peaks of CS found around ~1631 cm$^{-1}$ and of PVA around ~1421.35, ~1660 and ~1720 cm$^{-1}$ remained the same in the resulted blended CS/PVA composite nanofibers with slight shifting in the peaks, which is might be due to the physical interaction between the two materials.

Antibacterial Tests

Figure 6:
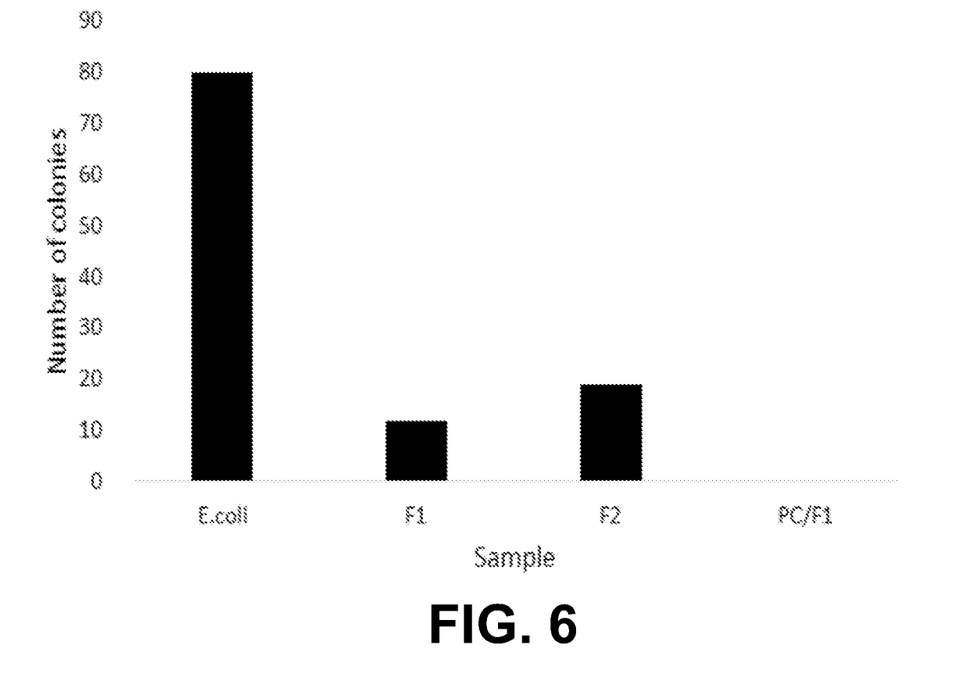
FIG. 6 shows according to an exemplary embodiment of the invention a histogram showing the number of colonies (CFU) of *E. coli* formed for each category i.e. *E. coli*, F1 (CA), F2 (AA), and PVA/CS/F1 nanofiber solution.
Figure 7:
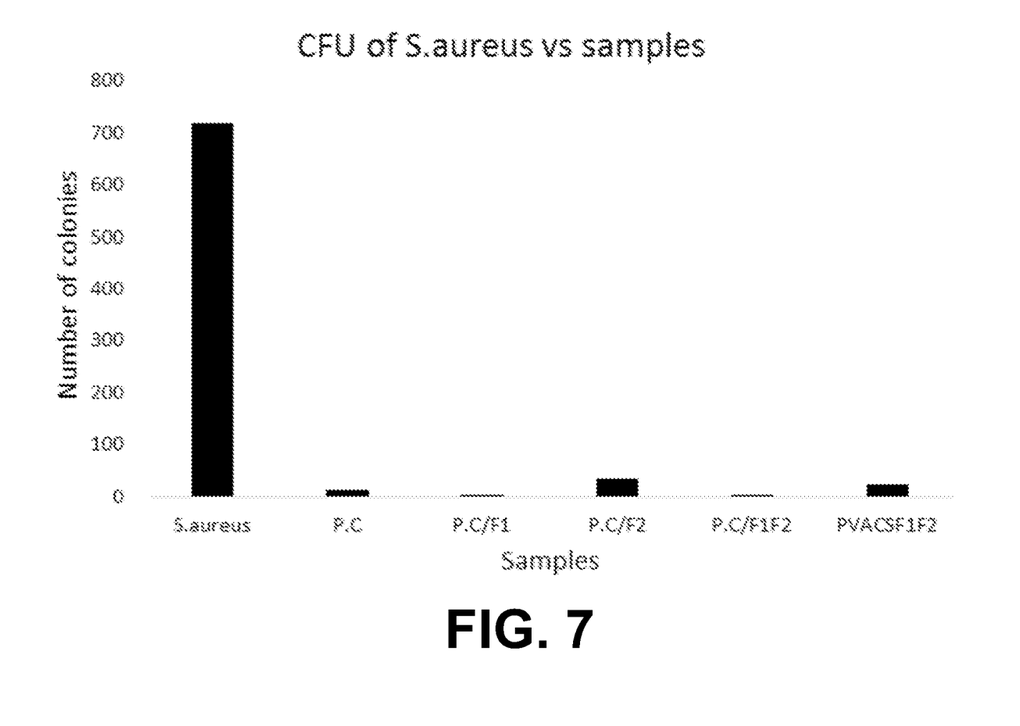
FIG. 7 shows according to an exemplary embodiment of the invention a histogram showing the number of colonies of S. aureus formed for PVA/CS nanofiber solution, PVA/CS/F1, nanofiber solution PVA/CS/F2 nanofiber solution, PVA/CS/F1+F2 nanofiber solution and pure PVA/CS/F1+F2 solution.
Figure 8A:
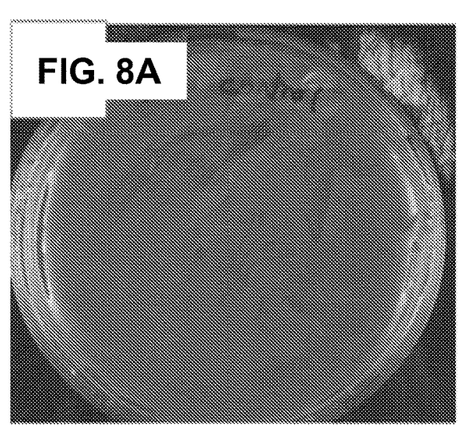
FIGS. 8A-D show according to an exemplary embodiment of the invention Images of bacterial culture FIG. 8A), and antibacterial activity of (FIG. 8B) Pure conventional disinfectant, (FIG. 8C) blank (FIG. 8D) 10/100 of disinfectant/0.4 g/100 mL nanofiber solution.
Figure 8B:
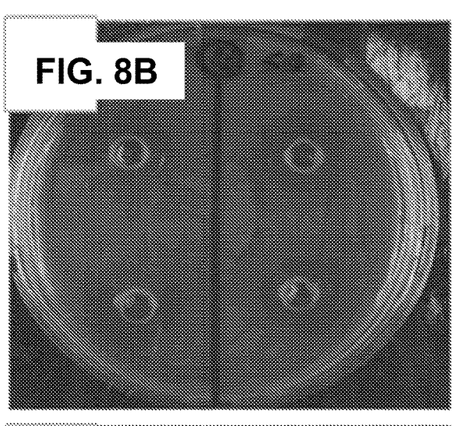
Figure 8C:
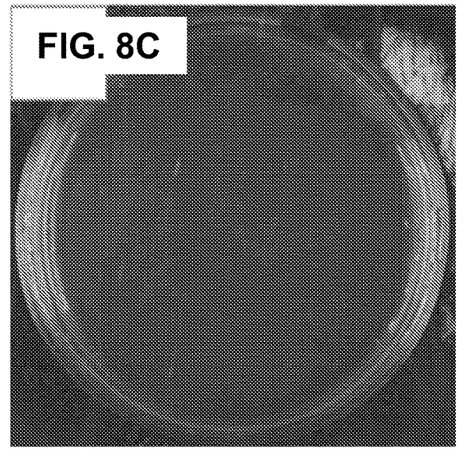
Figure 8D:
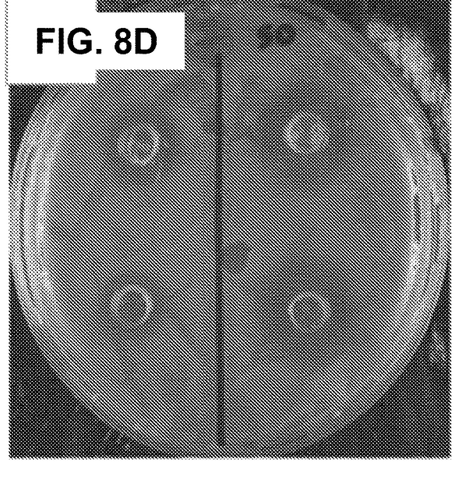

Antibacterial test carried out against *E. coli* and *S. aureus* was done by two methods; (a) serial dilution method and Inhibition zone examination for comparative analysis with conventional disinfectants. The results obtained (FIGS. 6 and 7) demonstrate strong antibacterial property of PVA/CS NFs and PVA/CS NFs solution mixed with CA and AA fillers. The antibacterial test proved similar efficiency against both Gram negative and Gram positive bacteria. Parent material (PVA/CS, CA, and AA) showed moderate activity against both strains of bacteria with PVA proving to be the weakest while PVA/CS showing moderate antibacterial activity and the two fillers (CA and AA) showing average activity against bacterial growth. When PVA/CS was electrospun to form nanofibers, the effect of antibacterial activity was enhanced by multiples of times and when the two fillers were added, the solution was able to clear out nearly 100% of the bacterial colonies.

Then, a separate study to examine the synergistic effect of the nanofibers formed when added to conventional disinfectant revealed a high performance for the composite nanofibers and the conventional disinfectant as compared with pure conventional disinfectant as shown in FIGS. 8A-D.

This study has shown that reducing the quantity of the conventional disinfectant by mixing it with a specific concentration of nanofiber solution enhances the clearance of bacteria from the surface more than when the pure conventional disinfectant was used for the same purpose even when the radius of interaction was nearly the same i.e. 18 mm on average. When this experiment was repeated using a lower concentration of nanofibers in combination with 1/10 of conventional disinfectant, a similar result showed in FIG. 6 was obtained.

Anticorrosion Test

Figure 9:
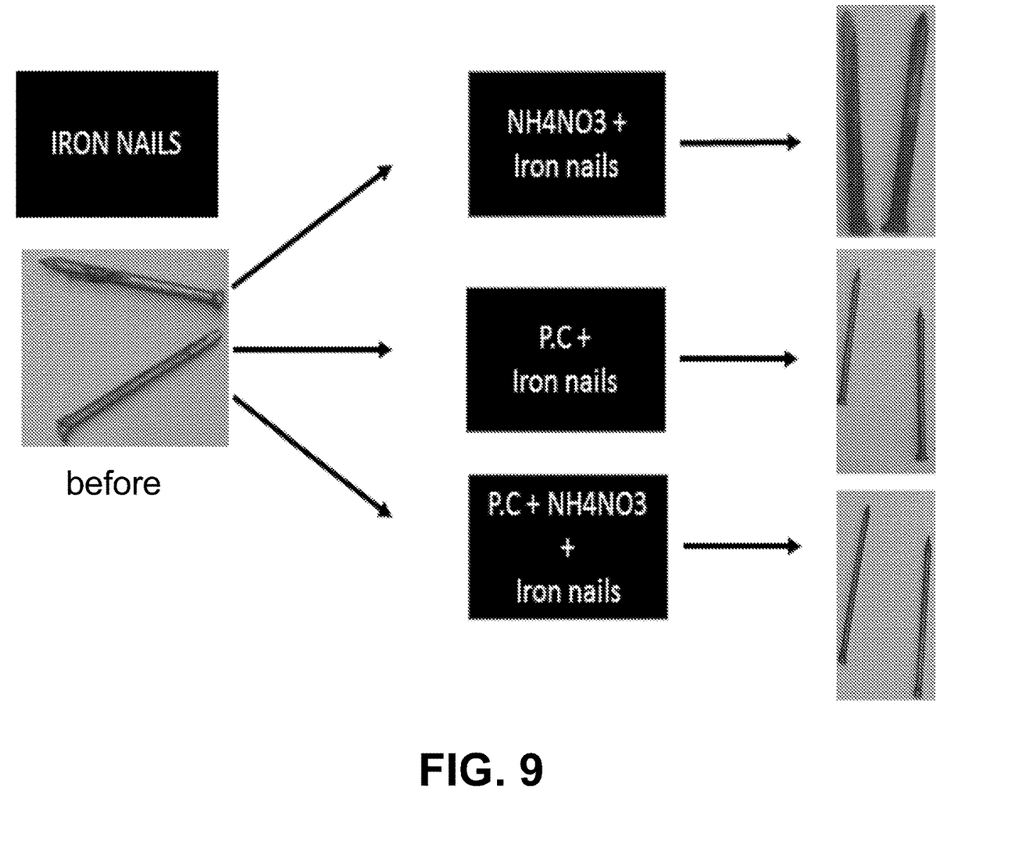
FIG. 9 shows according to an exemplary embodiment of the invention an image of iron nails before exposure to rust conditions (oxidizing agents), after exposure to $NH_4NO_3$, PVA/CS nanofiber (P.C.) solution, and a mixture of $NH_4NO_3$ and PVA/CS nanofiber (P.C.) solution.

After 24 hrs of exposure of iron nails to an oxidizing atmosphere ($NH_4NO_3$), water and PVA/CS nanofiber solutions, the results obtained showed tremendous ability of the PVA/CS nanofiber solution to prevent rusting as showed in FIG. 9. This results from the anti-oxidation properties of PVA/CS nanofiber solution prove its ability to prevent rust formation, and opens new avenues toward using Nanotechnology-based solutions for that purpose without sacrificing the high cost of replacing stainless steel production lines in the industrial sector due to rust formation.

CONCLUSION

With this embodiment, we showed the ability to produce smooth PVA/CS nanofibers and then successfully dissolved these nanofibers in CA and AA fillers solution to produce composite nanofiber solution. Thereafter, antibacterial properties of the nanofiber solutions were successfully examined. After careful manipulation of parameters, nanofibers with desirable properties were formed. Electrospinning PVA and CS composite polymers was one of the most challenging steps in the nanofiber synthesis as CS is polyanionic and therefore repels electric field making it difficult for the voltage to overcome electrostatic repulsion of CS. However, by reducing the ratio of CS in the composite, the PVA blends and shields CS from exposure and thereby enhancing the electrospinning process. Another crucial factor in this invention was to dissolve the composite nanofibers (PVA/CS) in solution while keeping the integrity and activity of the composite nanofibers. More importantly, another factor that was vital in this invention is adding two fillers (CA and AA) in order to add an addition anti-corrosion property to the composite nanofiber solution without affecting the other properties (like antibacterial) and have a final synergistic effect of all components together in a final solution form.

Testing the nanofibers against both gram positive and gram negative bacteria, it revealed equal killing capacity against both strains of bacteria. This capacity was even enhanced further with the introduction of CA and AA fillers, eliminating nearly 100% of the bacteria. CA proved more potent when combined with the PVA/CS nanofibers than with AA and when the two acids were combined together, there was a synergistic effect.

Applying the same concept to study the effect of nanofibers to the conventional disinfectant revealed that slight addition of the PVA/CS nanofibers to the conventional disinfectant, increases their potency by a very large margin. This is a very useful principle in the battle against environmental degradation by reducing the amount of chemicals applied in the formula. This can be extended to pesticides, insecticides, and antibiotics for reduction of dosage and maximization of the effect.

Converting the final composite nanofiber solutions including PVA/CS/CA/AA into different forms such as pressurized sprays, dry powder pads, or gels for example might open interesting channels towards the efficiency of such combination and the final form in a given application. More interestingly, applying these solutions of PVA/CS/CA/AA into different applications such as antifungal, spray for plants, bird repellents, mosquito repellents, and mixing it with chicken feed might reveal exciting advantages over using harsh chemicals in direct contact with plants, animals and humans.

What is claimed is:

1. A disinfectant, antibacterial and anticorrosion liquid, comprising:
    an electrospun solubilized nanofiber composition of natural chitosan (CS) and an FDA approved polymer polyvinyl alcohol (PVA), wherein the PVA and CS have a ratio of about 8:2, wherein the nanofiber composition is suspended or contained in a mixture of citric acid (CA), ascorbic acid (AA) and deionized water, wherein the CA and the AA are about 5% of the mixture, wherein the CS has a low molecular weight range, about 200 kDa and a degree of deacetylation of about 89.9% and wherein the natural chitosan is produced from shrimp shells.

2. The liquid composition as set forth in claim 1, wherein the PVA has a molecular weight of about 125000.

* * * * *